United States Patent
Haram

(10) Patent No.: US 12,108,963 B2
(45) Date of Patent: Oct. 8, 2024

(54) SURGICAL CUTTING TOOL

(71) Applicant: Norwegian University of Science and Technology, Trondheim (NO)

(72) Inventor: Per Magnus Haram, Trondheim (NO)

(73) Assignee: ST. OLAVS HOSPITAL, TRONDHEIM UNIVERSITY HOSPITAL, Trondheim (NO)

( * ) Notice: Subject to any disclaimer, the term of this patent is extended or adjusted under 35 U.S.C. 154(b) by 849 days.

(21) Appl. No.: 17/186,460

(22) Filed: Feb. 26, 2021

(65) Prior Publication Data
US 2021/0177450 A1    Jun. 17, 2021

Related U.S. Application Data

(63) Continuation of application No. PCT/EP2019/073088, filed on Aug. 29, 2019.

(30) Foreign Application Priority Data
Aug. 31, 2018    (GB) ...................... 1814219

(51) Int. Cl.
*A61B 17/32*    (2006.01)
*A61B 17/00*    (2006.01)

(52) U.S. Cl.
CPC .............. *A61B 17/32002* (2013.01); *A61B 2017/00477* (2013.01); *A61B 2017/320032* (2013.01)

(58) Field of Classification Search
CPC ..... A61B 17/14; A61B 17/142; A61B 17/144; A61B 17/147; A61B 17/148; A61B 17/32; A61B 17/32; A61B 17/00; A61B 34/20
See application file for complete search history.

(56) References Cited

U.S. PATENT DOCUMENTS

| | | | | |
|---|---|---|---|---|
| 5,201,749 A | * | 4/1993 | Sachse | A61B 17/144 606/177 |
| 9,060,783 B2 | | 6/2015 | Walen et al. | |
| 2005/0240193 A1 | | 10/2005 | Layne et al. | |
| 2006/0095046 A1 | | 5/2006 | Trieu et al. | |
| 2013/0150856 A1 | * | 6/2013 | Mimran | A61B 17/025 606/79 |

(Continued)

FOREIGN PATENT DOCUMENTS

| CN | 203852398 U | 10/2014 |
|---|---|---|
| CN | 104138289 A | 11/2014 |

(Continued)

OTHER PUBLICATIONS

International Search Report and Written Opinion received for International Application No. PCT/EP2019/073088, mailed on Oct. 31, 2019, 16 pages.

*Primary Examiner* — Christopher J Beccia
(74) *Attorney, Agent, or Firm* — Dorsey & Whitney LLP

(57) ABSTRACT

A surgical cutting tool for keyhole surgery comprises: a handle 2 at a proximal end of the tool; an elongate member 4 extending from the handle to a distal end of the tool; and a saw 6 at the distal end of the tool, the saw being supported by the elongate member 4. The elongate member 4 has a length allowing for insertion of the saw 6 into the body by a distance of at least 150 mm. The tool is arranged for insertion of the saw 6 into the body during keyhole surgery; and the saw 6 is able to cut bone when pressed against the bone.

17 Claims, 3 Drawing Sheets

(56) References Cited

U.S. PATENT DOCUMENTS

2014/0364890 A1  12/2014  Moody et al.
2015/0066032 A1   3/2015  Young
2017/0348034 A1  12/2017  Lapierre et al.

FOREIGN PATENT DOCUMENTS

| CN | 204016408 U   | 12/2014 |
| CN | 104138283 B   |  3/2016 |
| EP |   1582156 A1  | 10/2005 |
| GB |   2576876 A   |  3/2020 |
| WO | 2020043823 A1 |  3/2020 |

\* cited by examiner

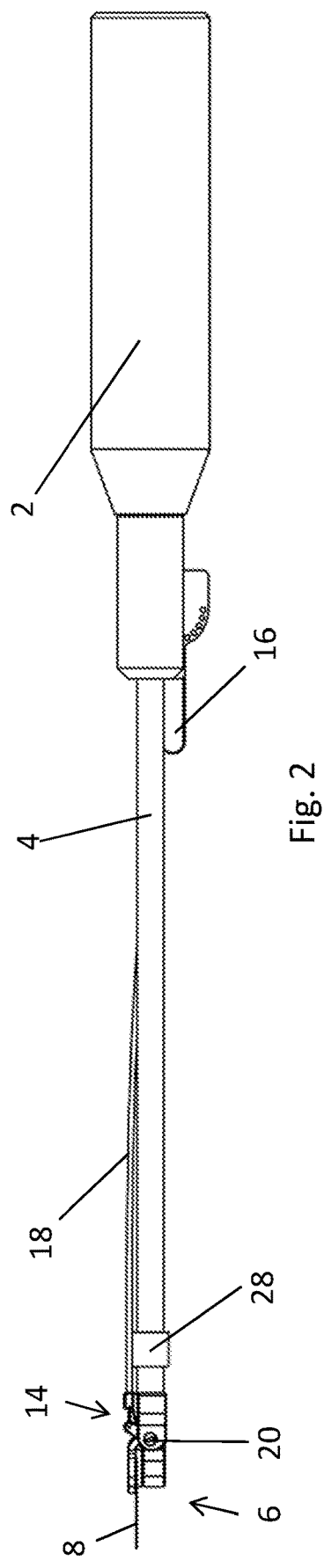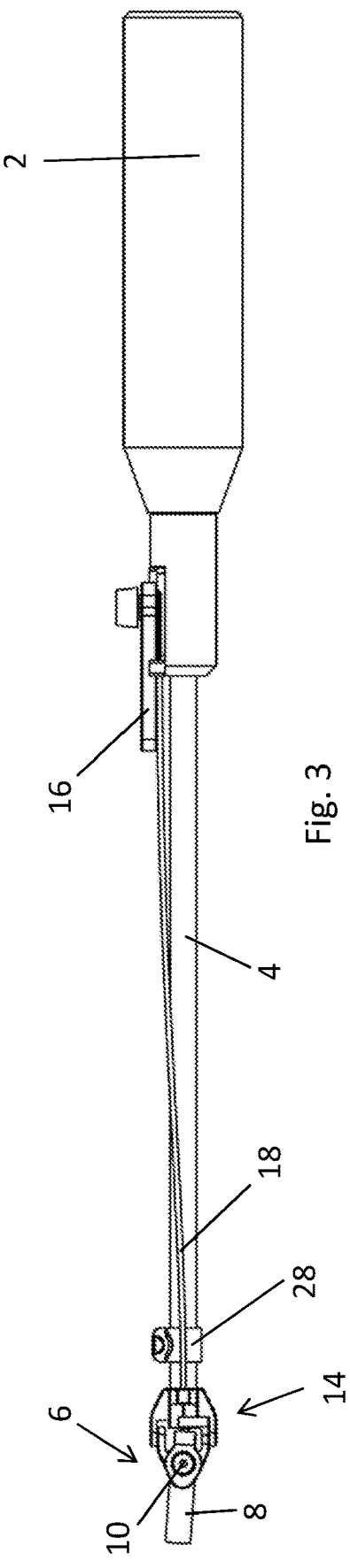

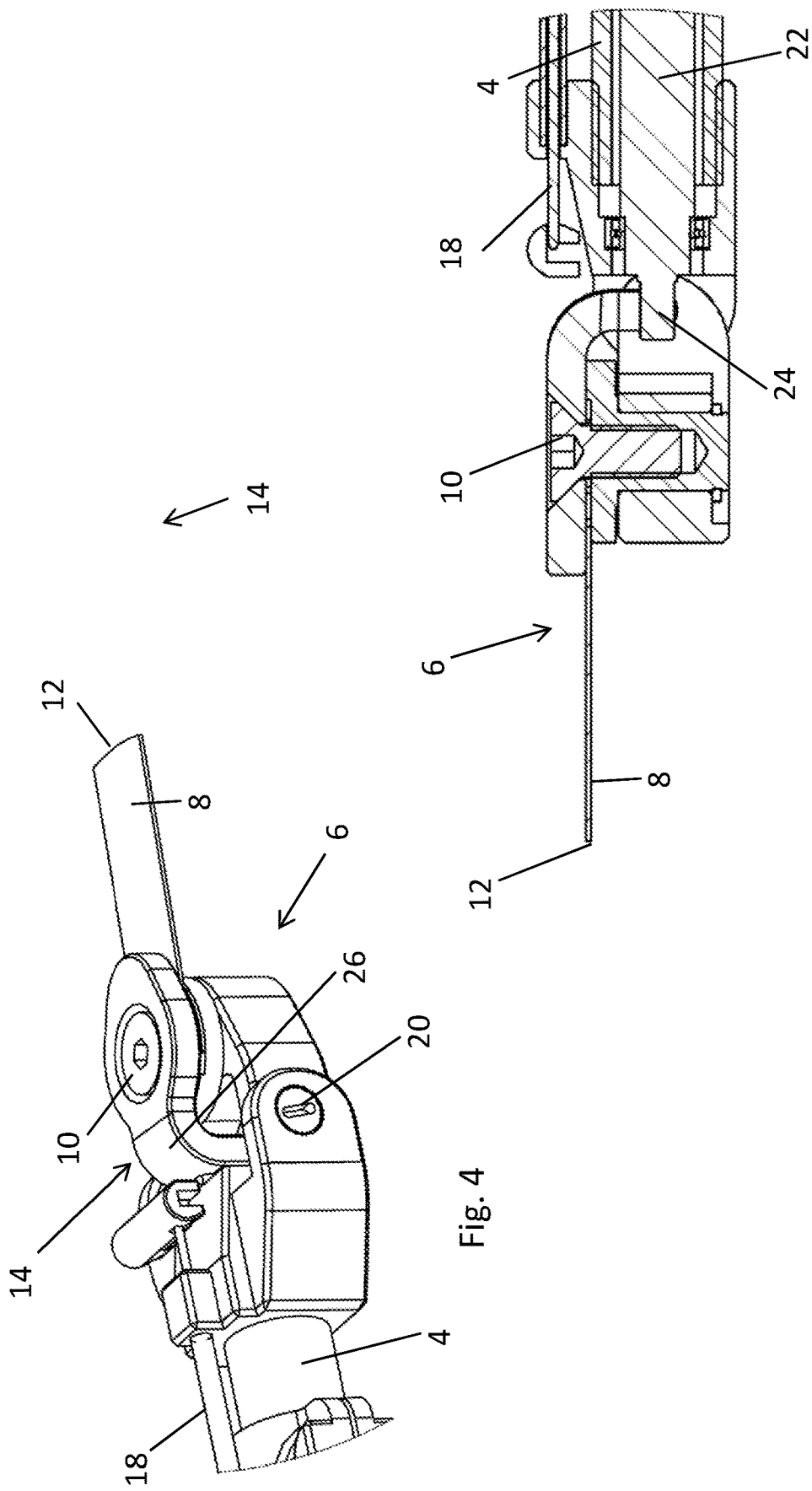

SURGICAL CUTTING TOOL

CROSS-REFERENCE TO RELATED APPLICATIONS

This application claims priority to International Patent Application No. PCT/EP2019/073088, filed Aug. 29, 2019, entitled "SURGICAL CUTTING TOOL," which in turn claims priority to United Kingdom Patent Application No. 1814219.0, filed Aug. 31, 2018, entitled "SURGICAL CUTTING TOOL", each of which is incorporated by reference herein, in the entirety and for all purposes.

TECHNICAL FIELD

Implementations relate to a surgical cutting tool, and in particular to a surgical cutting tool for cutting bones such as rib bones.

BACKGROUND

There are various circumstances in which a surgeon may wish to cut relatively hard objects such as bones during surgery. In conventional 'open' surgical procedures the surgeon can make use of various tools for cutting such objects, such as pliers, shears and saws, including manual saws as well as powered saws. In relation to powered surgical saws, devices exist with reciprocating, oscillating or rotating blades, as well as wire cutters and other systems, such as ultrasound based cutting systems for softer tissue types. One type of known device is a sagittal saw. A typical sagittal saw has a planar saw blade arranged with a cutting device at the distal end of the blade, and a handle at the proximal end of the saw blade. The handle usually houses a mechanism for actuating the cutting device, such as via movement of the whole blade or by movement of a cutter at the distal end of the blade, with the remainder of the blade staying motionless. An example of a sagittal saw of this type is disclosed in U.S. Pat. No. 9,060,783.

SUMMARY

Viewed from a first aspect, a surgical cutting tool for keyhole surgery is provided, the tool comprising: a handle at a proximal end of the tool; an elongate member extending from the handle to a distal end of the tool; and a saw at the distal end of the tool, the saw being supported by the elongate member; wherein the elongate member has a length allowing for insertion of the saw into the body by a distance of at least 150 mm; wherein the tool is arranged for insertion of the saw into the body during keyhole surgery; and wherein the saw is able to cut bone when pressed against the bone.

With this tool it becomes possible to use the saw during keyhole surgery, such as thoracoscopic surgery. Keyhole surgery which is a surgical technique in which operations are performed through relatively small incisions through the skin and body tissues, at points which are spaced apart from the site of the surgical operation. Keyhole surgery is also termed minimally invasive surgery (MIS) or bandaid surgery. It is well established that this type of surgery can have advantages to the patient compared to a more traditional open procedure. Keyhole surgery can be seen as a part of the broader field of endoscopy and it often includes the use of an endoscope type device allowing for remote viewing of the surgical operation using an optical fibre system or a camera system.

The inventors have realised that existing surgical cutting tools are not effective during this type of surgery, and thus they have identified a need for a new type of tool with an elongate member having a suitable length and the capability for use in keyhole surgery. Whilst known surgical saw devices such as the sagittal saws referenced above can allow the surgeon to operate some distance into the body, their length is not sufficient for keyhole surgery. Moreover, the form of the elongate blade of such saws is not suitable for use in keyhole surgery, as the sides of the blade would disrupt and/or damage body tissue that was not the subject of the surgery, as well as being unsuitable for entry into the body via openings of the type used for keyhole surgery.

It is possible to cut bones during keyhole surgery using existing tools, for example via the use of specialised long handled pliers to cut ribs using video assisted thoracoscopic surgery (VATS), there are potential complications to such procedures and risks to the patient. Scanlan International, Inc. of Minnesota, USA, offer a "rib cutter" tool for VATS. This rib cutter uses an anvil shear type cutting mechanism with the anvil fixed to an elongate rod and the cutting blade sliding along the rod so that a rib can be pressed between the blade and the anvil. However, these existing devices suffer from reduced maneuverability and restrictions on how they can be used compared to the proposed surgical cutting tool. For example, the known tools mentioned above cannot necessarily reach all ribs in the thoracic cavity during VATS. In contrast, the saw at the distal end of the cutting tool of the first aspect allows for straightforward cutting of bones and other hard objects during insertion of the tool via an opening as used for keyhole surgery, and this can be done via a simple and easily controlled movement of the tool. It is not necessary to have access to both sides of the bone or to approach the bone from a particular angle.

In some embodiments the elongate member has a length allowing for insertion of the cutter into the body by a distance of more than 150 mm, such as a distance of at least 200 mm, at least 250 mm or at least 300 mm. A suitable length allows for greater flexibility for the tool and the ability to reach across the body to the surgical site, for example to reach across the chest cavity to cut a rib. The length of the insertion of the cutter into the body may be defined as the distance from the exterior surface of the body at the point the tool enters the body up to the distal end of the cutter, i.e. the furthest distance along the tool from the entry point to the end of the cutter.

It will be appreciated that to allow for ease of use and maneuverability of the tool during surgery then the total length of the elongate member may be larger than the length of insertion, such that some proportion of its length can remain outside of the body and so that the handle of the tool does not need to be pressed against the body surface during full insertion of the cutter. Thus, the total length of the elongate member may be greater than the intended length of insertion by at least 100 mm, or at least 150 mm, or at least 200 mm. The total length of the tool will also exceed the insertion length by some amount. The total length of the tool may for example be at least 300 mm, at least 400 mm, or it may be 500 mm or more.

In order for the tool to be able to be used in keyhole surgery with minimal risk to the patient then the elongate member may have a rounded shape in cross-section. This is to be contrasted with the flat blade of a sagittal saw, which has edges that could cause damage to body tissue in some situations. The rounded shape of the elongate member may have no sharp edges, and could have a circular or oval cross-section, for example, or another prismatic cross-section with any edges rounded off. The elongate member may be an elongate tube or rod, such as a circular tube. The tool may be arranged such that the saw and elongate member may be inserted into an incision for keyhole surgery, such as an incision of less than 4 cm width, or less than 3 cm width. Thus, the largest width of the saw and/or the elongate member may be less than 4 cm, and in some implementations less than 3 cm.

In some example embodiments the elongate member is straight along its full length. However, it will be appreciated that as with other surgical tools then curved shapes may be provided for specialised applications, for example an elongate member that has a curve along some or all of its length in order to allow the tool to extend around obstructions within the body such as body organs.

The tool may include a collar located on the elongate member allowing for other tools to grip the elongate member, for example for stabilisation during cutting or to aid maneuverability of the tool as it advances toward or is removed from a cutting site. In addition, or alternatively, the tool may be adapted for use with a keyhole surgery port, i.e. a supportive port at the entry point to the body, and thus it may include features designed to interact with such a port.

The saw may comprise a cutting mechanism extending across a width of the distal end of the tool, such as a saw blade or wire. The cutting mechanism may extend transverse to the longitudinal axis of the elongate member for a width of up to 20 mm, such as a width of 10 mm or less. The cutting mechanism at the distal end allows the distal end of the tool to be pushed against an object to be cut, such as a bone, and to cut into the object as the saw is moved further toward and through the object via movement of the tool. In contrast to the known Scanlan rib cutter there is no need for an anvil or other part of the tool to be placed behind the bone during cutting. The saw may comprise a cutting mechanism of any suitable type, such as an oscillating saw blade, a wire type saw, a rotating disc saw, or a saw blade excited by vibrations from ultrasound or piezoelectric transducers. An oscillating saw blade may use any type of oscillation, such as a reciprocating blade with movement in a straight line or a blade with rotating oscillation. A rapidly oscillating saw provides an easily controlled cutting action that works well during keyhole surgery. It will be appreciated that saws for cutting bone are known in various designs, but that the cutting tool of the first aspect differs significantly from other surgical saw tools in that the saw is mounted via the elongate member and thereby sits a long way forward of the handle to allow for effective use in keyhole surgery.

The saw may be mounted to the elongate member with a pivoting joint in order to allow the angle of the cutting mechanism to vary relative to the longitudinal axis of the elongate member. This can permit easier access to some target sites, for example in the case of VATS it may allow for cutting of all ribs in a direction generally transverse to the ribs. The largest width of the pivoting joint may be less than 4 cm, and in some implementations less than 3 cm. The saw may include a blade section joined to the elongate member via the pivoting joint, with the cutting mechanism at a distal end of the blade section. With this arrangement, movement of the saw via the pivoting joint may result in angulation of the blade section relative to the longitudinal axis of the elongate member, with the blade section extending in a direction outward from the axis. In some examples the pivoting joint may allow for rotation of 45 degrees or more, such as rotation of 80 degrees or more.

The rotation of the pivoting joint may be able to occur in both a clockwise and an anticlockwise direction away from alignment with the longitudinal axis of the elongate member, or in some cases the pivoting mechanism may be arranged for rotation in one direction only. It will be understood that rotation in two directions may not be necessary since the tool can be twisted with a rotation of the elongate member in order to move the angulated saw into any required position. The pivoting mechanism may be actuated by a wire or rod. If tension is used to actuate the pivoting mechanism then a spring return may be provided to restore the pivoting mechanism, with the attached saw, to a resting position. The resting position may have the saw aligned with the longitudinal axis of the elongate member, i.e. with the saw blade (where present) lying along the longitudinal axis of the elongate member. The tool may include a lever arm for actuating the rotation of the pivoting joint, for example by applying force to the wire or rod. The lever arm may be fixed to the handle.

Whilst example embodiments use a pivoting joint to allow for varying angulation of the saw, it is also possible to use a fixed saw. In one advantageous arrangement the saw may be fixed and may extend forward from the distal end of the elongate member at an angle of 45 degrees to the longitudinal axis of the elongate member. Such an arrangement simplifies the device by allow omission of the pivoting joint whilst maintaining some flexibility to approach bones at varying angles relative to the entry point during keyhole surgery. However, the trade-off is that more care may be required when inserting the saw into the body and whilst manoeuvring the tool during surgery.

The tool may include a twisting mechanism allowing for the saw to be rotated in a twisting motion relative to the handle, with rotation of the saw around a longitudinal axis of the handle. The saw may rotate along with the elongate member, with the twisting mechanism hence including parts at the point where the elongate member joins to the handle. It is useful to be able to twist the handle relative to the saw as this allows for the handle to be placed in the most convenient orientation for access to the grip and motor controls, as well as to an actuating mechanism for the pivoting joint, where present. The twisting mechanism may include a lock that engages to fix the twisting orientation of the saw relative to the handle, and that can be disengaged to permit twisting rotation of the saw, and optionally of the elongate member, relative to the handle. The lock might allow for twisting movement to any position, or in some examples it allows a set number of positions of the saw relative to the handle, such as 8 or 12 positions.

In one example the saw, such as an oscillating saw blade with a cutting edge at a distal end thereof, is driven by a motor, such as a linear motor or a motor with a rotating drive system. The motor may be housed in the handle, or alternatively it may be located at the distal end of the tool close to the saw. An electrical or pneumatic system may be used. In the case of an electrical motor then the tool may include a connection to receive power from an external source or it may include a battery for powering the electrical motor. A battery may be housed within the handle. A pneumatically powered tool may include a connection to couple the tool to a pneumatic system providing an appropriate air pressure, with a suitable pneumatic drive for the saw. In one example the motor is in the handle and kinetic energy is transferred to the saw via a shaft within the elongate member, such as a rotating shaft.

One example implementation includes an oscillating saw blade that is oscillated by energy transferred along the elongate member via a rotating shaft, with the oscillating movement of the saw blade being generated via an offset pin at the end of the shaft. The offset pin may be coupled to the saw blade via a connector with a slot extending perpendicular to the shaft, such that rotation of the shaft rotates the pin to move it up and down the slot whilst the slot oscillates side-to-side, resulting in an oscillating movement of the connector. This oscillating movement can be transferred to the saw blade by suitable coupling of the connector to the saw blade. For example, they may be rigidly attached to one another about a pivot point and both extending outward from the axis of rotation of the pivot, so that oscillating movement of the connector at one side of the pivot point leads to corresponding oscillating movement of the saw blade at the other side, generating an oscillating movement of saw teeth at the end of the saw blade.

As discussed above, the surgical cutting tool may be specifically adapted for keyhole surgery. It is expected that the tool will have particular benefits when used for thoracoscopic surgery and in particular video assisted thoracoscopic surgery (VATS), but the tool may also provide benefits in a wider context, such as for laparoscopic surgery and other endoscopic procedures. The tool may be arranged for use in such surgical procedures. In some examples the tool is adapted for use with robotic surgery systems and thus may include connectors and/or navigation systems as required for use in a robotic surgery system. Implementations of the present disclosure may thus extend to a robotic surgery device including a cutting tool as discussed above.

Implementations may further extend to the use of the surgical cutting tool, for example for cutting bone. This may include use in keyhole surgery and in particular use in thoracoscopic surgery, such as for cutting ribs. The use may involve surgery of the animal or human body. A method including use of the surgical cutting tool may include using a tool with any of the other features set out above.

BRIEF DESCRIPTION OF THE DRAWINGS

An example implementation of the present disclosure will now be described by way of example only and with reference to the accompanying drawings, in which:

FIGS. 2 and 3 are side and top views of the cutting tool of FIG. 1;

FIG. 4 is a close up view of a saw at the distal end of the cutting tool; and FIG. 5 shows a cross-section of the distal end of the cutting tool.

DETAILED DESCRIPTION

Figure 1:
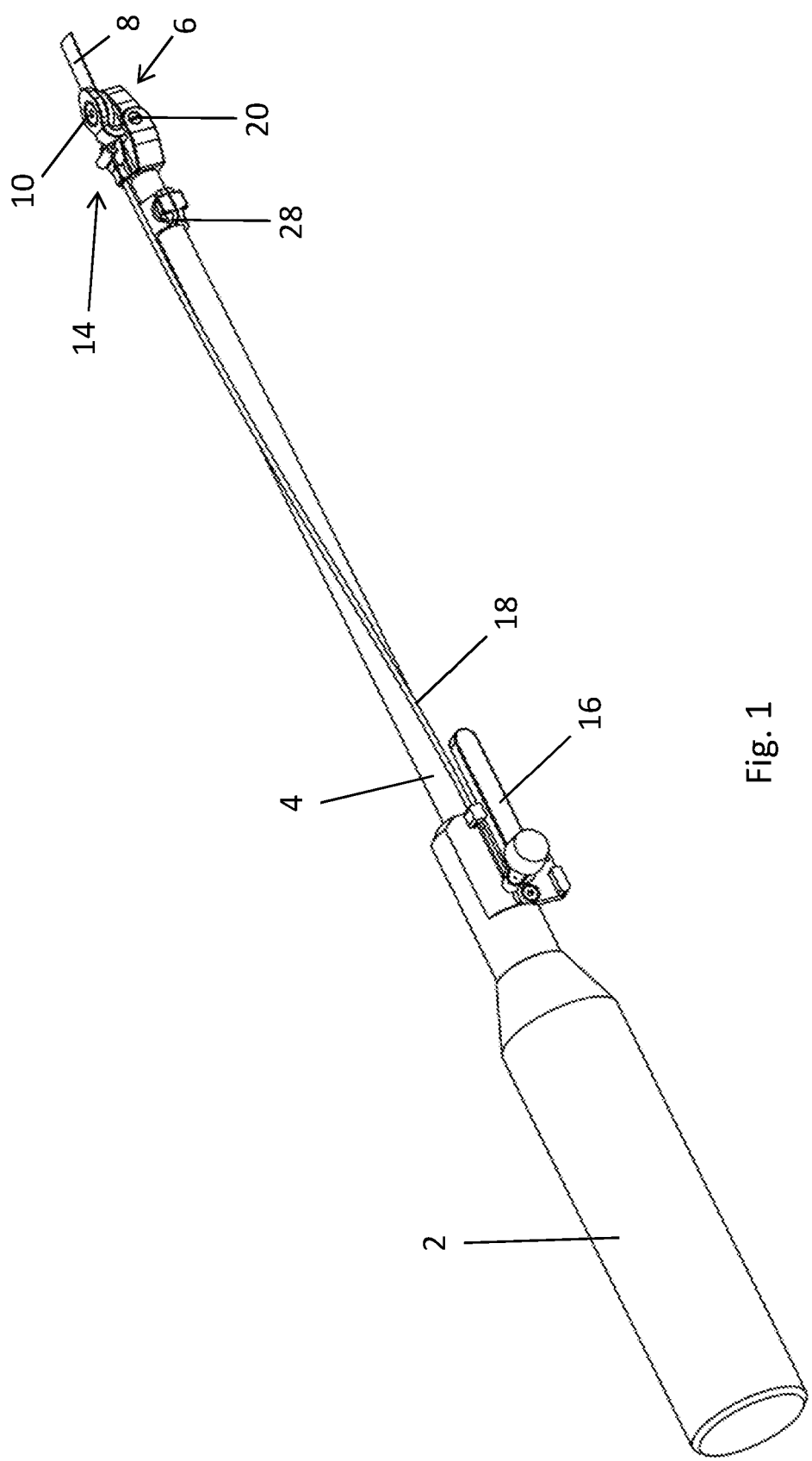
FIG. 1 shows a perspective view of a surgical cutting tool for keyhole surgery.

The Figures show a surgical cutting tool that may be used for cutting ribs during for keyhole surgery. It has been found that there is a need for such a tool in order to enable continued development of improved surgical techniques. For example, in the treatment of intrathoracal disease such as lung cancer, a thoracotomy was traditionally done to gain access to intrathoracal organs. A thoracotomy can be done in several ways, but always involves dividing extrathoracal musculature and expanding the intercostal space with a retractor. This gives an excellent access to the intrathoracic organs, but yields high morbidity. Thoracotomies are painful and patients exposed to this type of surgical procedure need 10-14 days in hospital because of disability and pain.

To reduce the amount of thoracotomy-related complications, surgeons started to do the intrathoracal surgery with scopic techniques (i.e. keyhole surgery), also called VATS (Video Assisted Thoracoscopic Surgery) around 1990. In VATS, 1-3 small incisions are made. These are never larger than 4-5 cm. Muscles are never divided, and retractors are never used. This results in less pain and a recovery time that is reduced to 3-4 days. At first, the procedures done with VATS were relatively simple and complaints of difficulties in access halted the evolution from simple to more complex operations. In more recent times, aided by the development in fibre optics and more versatile equipment, more complex procedures can be carried out by VATS. Complex cancer operations are now done with VATS at equal oncologic radicality and safety as by conventional thoracotomy. Although some operations still have to be done with a conventional thoracotomy, leading centres worldwide generally conduct more than 80% of the thoracic surgery by VATS technique.

There has been great progress in the technology of cutting and sealing of soft tissue, making VATS more feasible and safe. Conventional instruments like knife, scissors and suture are hardly needed when performing VATS on intrathoracic organs. However, the inventors' have found that developments have not included thoracic surgery involving bones. Expanding the VATS toolbox to include bone instruments is expected will make this kind of surgery less traumatic, yield less morbidity and pain and shorten the hospital stay.

It will be appreciated that the proposed tool can be put to use in any context where the surgeon sees benefits, including for veterinary treatment of animals as well as surgery on human patients. In addition to cutting ribs, the tool might be used during hip surgery, for example. However, particular benefits are seen in allowing for thoracoscopic surgery to include cutting of bones using this type of tool. There are several situations where you have to address bones in thoracic surgery. When lung cancer infiltrates one or more of the ribs, a part of one or several ribs have to be excised as a part of a more complex surgical procedure. There are also situations where the ribs are the only target for the surgery, such as primary tumours of the ribs and painful chronic fractures (pseudoarthrosis).

As seen in the Figures, and with initial reference to FIGS. 1, 2 and 3, the proposed surgical cutting tool in one example includes a handle 2 at its proximal end, the handle 2 holding an elongate member 4 that extends forward of the handle 2. A saw 6 is supported at the distal end of the elongate member 4. The elongate member 4 can take the form of a tube as shown, and it has a length suitable for providing access to objects such as bones requiring cutting during thoracoscopic surgery. In this example the elongate member 4 has a length sufficient to allow for about 330 mm of the tool to be within the body, e.g. within a port of a keyhole surgery system, and the tool as a whole has a total length of about 580 mm.

The saw 6 may use an oscillating saw blade 8 as shown, with the blade 8 mounted for oscillating rotation about a pivot 10. The tip 12 of the blade 8 forms the cutting edge and this may take any suitable form for cutting through bone and the like, such as including saw teeth or a sharpened profile. A rapidly oscillating saw blade offers an easily controlled sawing action. Because of this, these saws are widely used in orthopedic surgery and conventional thoracic surgery. Existing saws are compact machines where the cutting action is close to the engine and to the hands of the surgeon. In contrast to such known saws the proposed arrangement, using a tool with an elongate member 4 supporting the saw 6, allows for the sawing action to take place at a distance from the surgeons hands, as is required for thoracoscopic surgery and similar procedures, where the surgeons hands are never in contact with the surgical field. The surgeon sees the operating field on a screen with the camera or a lens thereof inside the thorax.

To allow for the saw 6 to easily access all ribs in the thorax, the tool in this example includes a pivoting joint 14 to vary angle of the saw blade 8. This can be seen in FIGS. 1-3 and it is shown in more detail in the close-up view of FIG. 4. By adjusting a lever arm 16 at the handle 2, a wire 18 can pull the saw 6 so that the saw blade 8 moves out of alignment with a longitudinal axis of the elongate member 4 by up to 80 degrees. The saw 6 rotates around a hinge point 20, which is formed by two U-shaped brackets, one attached to the elongate member 4 and one holding the saw 6. The U-shaped brackets oppose one another and overlap at the end of each U-shape, with the hinge 20 formed by pivots at each side. A spring return can be used to urge the saw 6 back to its resting position when the lever 16 is released. Alternatively the wire 18 may operate in tension and in compression so that it can both pull and push during the pivoting movement of the saw 6. The wire 18 runs within a casing or sheath as best seen in FIGS. 4 and 5.

In order to permit the saw 6 to take different orientations relative to the handle 2 then a twisting mechanism X1 is used at the point where the elongate member 4 joins to the handle 2. The twisting mechanism X1 allows the saw 6 and the elongate member 4 to rotate about the longitudinal axis of the tool relative to the handle 2. This allows the handle 2 to be placed in the most convenient orientation for access to a grip portion with the motor controls, as well as for access to the lever arm 16. Thus, the handle 2 might always take the same orientation outside of the body with different orientations of the saw within the body. In order to control the twisting movement then a lock is included for fixing the relative position of the handle and elongate member when required. The lock can permit rotation to a number of pre-set positions, for example to 8 or 12 positions.

The oscillating saw blade 8 at the tip of the saw 6 can be driven by an electric motor within the handle 2. A battery pack for the motor can also be within the handle 2. In this example, the motor rotates a drive shaft 22 inside the tubing of the elongate member 4, as shown in FIG. 5. An off-centre pin 24 on the end of the drive shaft sits in slot formed by a forked end of a connector 26 which is mounted to the saw blade 8 at the pivot 10. When the off-centre pin 24 rotates with the shaft 22 then it moves back and forth within the slot whilst moving the forked end of the connector 26 side-to-side in a direction transverse to the length of the shaft 22. This creates an oscillating action at the tip 12 of the saw blade 8. The use of the connector 26 with its forked end also allows for the saw 6 to pivot around the hinged joint 20 whilst maintaining the mechanical connection of the off-centre pin 24 with the connector 26. That means that the oscillating saw blade can be powered in the same way even as the angle of the saw blade 8 is changed by the pivoting joint 14.

The tool is designed to fit through an incision with a maximum width of 4 cm and to be manoeuvre within the body whilst it is inserted via such an incision. The diameter of the tube that forms the elongate member 4 may be 10 mm, and the maximum width of the pivoting joint 14 may be 25 mm. The saw blade 8 may be no wider than the thickness of a rib, i.e. 10 mm or less. The length of the saw blade 8 from the pivot 10 can be about 30 mm, which means that the cutting edge 12 moves in an arc of 30 mm radius during the oscillating motion.

The tool further includes a collar 28 mounted to the elongate member 4 in order to allow for another tool to grip and manipulate the elongate member 4, such as for stabilisation during cutting. In a variation that is not shown, the tool may alternatively or additionally be adapted for use with a keyhole surgery port, i.e. a supportive port at the entry point to the body, and thus it may include features designed to interact with such a port such as a further collar or connector. The use of the tool can include various types of operation as explained above as well as including manual handling or automated handling such as with a robotic surgery system.

What is claimed is:

1. A surgical cutting tool for keyhole surgery, the tool comprising:
   a handle at a proximal end of the tool;
   an elongate member extending from the handle to a distal end of the tool; and
   a saw at the distal end of the tool, the saw being supported by the elongate member, wherein the saw includes an oscillating saw blade that is oscillated by energy transferred along the elongate member via a rotating shaft, with oscillating movement of the saw blade being generated via an offset pin protruding from an end of the shaft at a distal end of the elongate member, wherein the offset pin is coupled to the saw blade via a connector with a slot extending perpendicular to the shaft, such that rotation of the shaft rotates the pin to move the pin up and down the slot while the slot oscillates side-to-side, resulting in an oscillating movement of the connector,
   wherein the tool is arranged for insertion of the saw into the body during keyhole surgery, and
   wherein the saw is able to cut bone when pressed against the bone.

2. The surgical cutting tool as claimed in claim 1, wherein the elongate member has a length allowing for insertion of a cutter into the body by a distance of at least 250 mm.

3. The surgical cutting tool as claimed in claim 1, wherein a total length of the tool is at least 400 mm.

4. The surgical cutting tool as claimed in claim 1, wherein the elongate member has a rounded shape in cross-section.

5. The surgical cutting tool as claimed in claim 4, wherein the elongate member is an elongate tube or rod.

6. The surgical cutting tool as claimed in claim 1, wherein a largest width of the saw and/or the elongate member is less than 4 cm.

7. The surgical cutting tool as claimed in claim 1, wherein the tool includes a collar located on the elongate member configured for other tools to grip the elongate member.

8. The surgical cutting tool as claimed in claim 1, wherein the tool is adapted for use with a keyhole surgery port.

9. The surgical cutting tool as claimed in claim 1, wherein the saw comprises a cutting mechanism extending across a width of the distal end of the tool.

10. The surgical cutting tool as claimed in claim 1, wherein the saw is mounted to the elongate member with a pivoting joint in order to allow an angle of a cutting mechanism of the saw to vary relative to a longitudinal axis of the elongate member.

11. The surgical cutting tool as claimed in claim 10, wherein the saw includes a blade section joined to the elongate member via the pivoting joint, with the cutting mechanism at a distal end of the blade section, such that movement of the saw via the pivoting joint will result in angulation of the blade section relative to the longitudinal axis of the elongate member with the angulated blade section extending in a direction outward from that axis.

12. The surgical cutting tool as claimed in claim 10, wherein the pivoting joint allows for rotation of 45 degrees or more.

13. The surgical cutting tool as claimed in claim 1, further comprising a twisting mechanism allowing for the saw to be rotated in a twisting motion relative to the handle, with rotation of the saw around a longitudinal axis of the handle.

14. The surgical cutting tool as claimed in claim 1, wherein the saw is driven by a motor in the handle, and wherein kinetic energy is transferred to the saw via the shaft, wherein the shaft is within the elongate member.

15. A robotic surgery device including a cutting tool as claimed claim 1.

16. A method comprising use of the surgical cutting tool of claim 1.

17. The method as claimed in claim 16, further comprising use of the tool for cutting ribs during thoracoscopic surgery.

* * * * *